US007521535B2

(12) United States Patent (10) Patent No.: US 7,521,535 B2
Zhang et al. (45) Date of Patent: Apr. 21, 2009

(54) ANTI-MICROBIAL DEFENSIN-RELATED PEPTIDES AND METHODS OF USE

(75) Inventors: Guolong Zhang, Stillwater, OK (US); Amar A. Patil, Roseland, NJ (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 0 days.

(21) Appl. No.: 11/857,048

(22) Filed: Sep. 18, 2007

(65) Prior Publication Data

US 2008/0076716 A1 Mar. 27, 2008

Related U.S. Application Data

(60) Provisional application No. 60/846,030, filed on Sep. 20, 2006.

(51) Int. Cl.
 *C07K 14/47* (2006.01)
 *A61K 38/17* (2006.01)
(52) U.S. Cl. .............................. 530/350; 514/2; 514/12
(58) Field of Classification Search ....................... None
 See application file for complete search history.

(56) References Cited

U.S. PATENT DOCUMENTS 5,530,109 A 6/1996 Goodearl et al.
 2008/0119405 A1 5/2008 Zhang et al.

FOREIGN PATENT DOCUMENTS

WO PCT/US07/78928 9/2007

OTHER PUBLICATIONS

Anderson et al., "Factors Affecting the Antimicrobial Activity of Ovine-Derived Cathelicidins Against *E. coli* 0157:H7," *International Journal of Antimicrobial Agents*, 2005, pp. 205-210, vol. 25, Publisher: Elsevier.
Ayabe et al., "Activation of Paneth Cell α-Defensins in Mouse Small Intestine," *The Journal of Biological Chemistry*, Feb. 15, 2002, pp. 5219-5228, vol. 277, No. 7, Publisher: The American Society for Biochemistry and Molecular Biology.
Bowdish et al., "Impact of LL-37 on Anti-Infective Immunity," *Journal of Leukocyte Biology*, 2005, pp. 451-459, vol. 77, Publisher: Society for Leukocyte Biology.
Darmoul et al., "Positional Specificity if Defensin Gene Expression Reveals Paneth Cell Heterogeniety in Mouse Small Intestine," *The American Physiological Society*, 1996.
Finch, "Antibiotic Resistance: A View From the Prescriber," *Nature Reviews: Microbiology*, 2004, pp. 989-994, vol. 2.
Friedrich et al., "Salt-Resistant Alpha-Helical Cationic Antimicrobial Peptides," *Antimicrobial Agents and Chemotherapy*, 1999, pp. 1542-1548, Publisher: American Society for Microbiology.
Froy et al., "Arthropod and Mollusk Defensins—Evolution by Exon-Shuffling," *Trends in Genetics*, 2003, pp. 684-687, vol. 19, No. 12.
Ganz, "Defensins: Antimicrobial Peptides of Innate Immunity," www.nature.com/reviews/immunol, 2003, pp. 710-720, vol. 3, Publisher: Nature Publishing Group.

Ghosh et al., "Paneth Cell Trypsin is the Processing Enzyme for Human Defensin-5," www.immunol.nature.com, May 20, 2002, pp. 583-590, vol. 3, No. 6, Publisher: Nature Publishing Group.
Goldman et al., "Human β-Defensin-1 is a Salt-Sensitive Antibiotic in Lung That is Inactivated in Cystic Fibrosis," *Cell*, Feb. 21, 1007, pp. 553-560, vol. 88, Publisher: Cell Press.
Gonzalez et al., "Excessive Antibiotic Use for Acute Respiratory Infections in the United States," *Clinical Infectious Diseases*, 2001, pp. 757-762, vol. 33, Publisher: Infectious Diseases Society of America.
Hancock et al., "The Role of Antimicrobial Peptides in Animal Defenses," *PNAS*, Aug. 1, 2000, pp. 8856-8861, vol. 97, No. 16.
Hornef et al., "Increased Diversity of Intestinal Antimicrobial Peptides by Covalent Dimer Formation," *Nature Immunology*, 2004, pp. 836-843, vol. 5, No. 8, Publisher: Nature Publishing Group.
Huttner et al., "A Family of Defensin-Like Genes Codes for Diverse Cysteine-Rich Peptides in Mouse Paneth Cells," *Genomics*, 1994, pp. 99-109, vol. 24, Publisher: Academic Press.
Koprivnjak et al., "Cation-Induced Transcriptional Regulation of the dlt Operon of *Staphylococcus aureus*," *Journal of Bacteriology*, 2006, pp. 3622-3630, vol. 188, No. 10, Publisher: American Society for Microbiology.
Krishnakumari et al., "Antibacterial Activities of Synthetic Peptides Corresponding to the Carboxy-Terminal Region of Human β-Defensins 1-3," *Peptides*, 2006, pp. 2607-2613, vol. 27, Publisher: Elsevier.
Lehrer, "Primate Defensins," *Nature Reviews: Microbiology*, 2004, pp. 727-738, vol. 2.
Lehrer et al., "Modulation of the in Vitro Candidacidal Activity of Human Neutrophil Defensins by Target Cell Metabolism and Divalent Cations," *J. Clin. Invest.*, 1988, pp. 1829-1835, vol. 81, Publisher: The American Society for Clinical Investigations.
Lehrer et al., "Defensins of Vertebrate Animals," *Current Opinion in Immunology*, 2002, pp. 96-102, vol. 14, Publisher: Elsevier
McPhee et al., "Function and Therapeutic Potential of Host Defence Peptides," *Journal of Peptide Science*, 2005, pp. 677-687, vol. 11, Publisher: Wiley InterScience.
Miller et al., "Effects of Osmotic Gradients on Water and Solute Transport: In Vivo Studies in Rat Duodenum and Ileum," 1979, Publisher: The American Physiological Society.
Ouellette, "Defensin-Mediated Innate Immunity in the Small Intestine," *Best Practice & Research Clinical Gastroenterology*, 2004, pp. 405-419, vol. 18, No. 2, Publisher: Elsevier.
Ouellette et al., "Peptide Localization and Gene Structure of Cryptdin 4, A Differentially Expressed Mouse Paneth Cell α-Defensin," *Infection and Immunity*, 1999, pp. 6643-6651, vol. 67, No. 12, Publisher: American Society for Microbiology.

(Continued)

*Primary Examiner*—Prema Mertz
(74) *Attorney, Agent, or Firm*—Fellers, Snider, Blankship, Bailey & Tippens

(57) ABSTRACT

An antimicrobial peptide and its analogs that are insensitive to physiological salt and divalent cation concentrations is provided, as are methods for their use to treat and prevent bacterial infections. The peptides are especially useful to treat infections caused by bacteria that are resistant to traditional antibiotic therapy.

8 Claims, 8 Drawing Sheets

OTHER PUBLICATIONS

Ouellette et al., "A Novel Mouse Gene Family Coding for Cationic, Cysteine-Rich Peptides," *The Journal of Biological Chemistry*, 1990, pp. 9831-9837, vol. 265, No. 17, Publisher: The American Society for Biochemistry and Molecular Biology.

Patil et al., "Rapid Evolution and Diversification of Mammalian α-Defensins as Revealed by Comparative Analysis of Rodent and Primate Genes," *Physiol Genomics*, Oct. 19, 2004, pp. 1-11, vol. 20, Publisher: The American Physiological Society.

Patil et al., "Cross-Species Analysis of the Mammalian β-Defensin Gene Family: Presence of Snytenic Gene Clusters and Preferential Expression in the Male Reproductive Tract," *Physiol Genomics*, Jul. 20, 2005, pp. 5-17, vol. 23, Publisher: The American Physiological Society.

Peyrin-Biroulet et al, "Nods in Defence: From Vulnerable Antimicrobial Peptides to Chronic Inflammation," *Trends in Microbiology*, 2006, vol. 14, No. 10, Publisher: Elsevier.

Porter et al., "Broad-Spectrum Antimicrobial Activity of Human Intestinal Defensin 5," *Infection and Immunity*, 1997, pp. 2396-2401, vol. 65, No. 6, Publisher: American Society for Microbiology.

Raj et al., "Large-Scale Synthesis and Functional Elements for the Antimicrobial Activity of Defensins," *Biochem. J.*, 2000, pp. 633-641, vol. 347, Publisher: Biochemical Society.

Salzman et al., "Paneth Cells, Defensins, and the Commensal Microbiota: A Hypothesis on Intimate Interplay at the Intestinal Mucosa," *Seminars in Immunology*, 2007, pp. 70-83, vol. 19, Publisher: Elsevier.

Satchell et al., "Quantitative Interactions Between Cryptidin-4 Amino Terminal Variants and Membranes," *Peptides*, 2003, pp. 1795-1805, vol. 24, Publisher: Elsevier.

Satchell et al., "Interactions of Mouse Paneth Cell α-Defensins and α-Defensin Precursors With Membranes," *The Journal of Biological Chemistry*, Apr. 18, 2003, pp. 13838-13846, vol. 278, No. 16, Publisher: The American Society for Biochemistry and Molecular Biology.

Schibli et al., "The Solution Structures of the Human β-Defensins Lead to a Better Understanding of the Potent Bactericidal Activity of HBD3 Against *Staphylococcus aureus*," *The Journal of Biological Chemistry*, Mar. 8, 2002, pp. 8279-8289, vol. 277, No. 10, Publisher: The American Society for Biochemistry and Molecular Biology.

Selsted et al., "Mammalian Defensins in the Antimicrobial Immune Response," *Nature Immunology*, 2005, pp. 551-557, vol. 6, No. 6.

Shirafuji et al., "Structural Determinants of Procryptdin Recognition and Cleavage by Matrix Metalloproteinase-7," *The Journal of Biological Chemistry*, Mar. 7, 2003, pp. 7910-1919, vol. 278, No. 10, Publisher: The American Society for Biochemistry and Molecular Biology.

Tanabe et al., "Structure-Activity Determinants in Paneth Cell α-Defensins," *The Journal of Biological Chemistry*, 2004, pp. 11976-11983, vol. 279, No. 12, Publisher: The American Society for Biochemistry and Molecular Biology.

Thomma et al., "Plant Defensins," *Planta*, 2002, pp. 193-202, vol. 216, Publisher: Springer-Verlag.

Wehkamp et al., "Paneth Cell Antimicrobial Peptides: Topographical Distribution and Quantification in Human Gastrointestinal Tissues," *FEBS Letters*, 2006, pp. 5344-5350, vol. 580, Publisher: Elsevier.

Wilson, "Regulation of Intestinal α-Definsin Activation by the Metalloproteinase Matrilysin in Innate Host Defense," *Science*, 1999, pp. 113-117, vol. 286.

Wu et al., "Productive Folding of Human Neutrophil α-Defensins in Vitro Without the Pro-Peptide," *J. Am. Chem. Soc.*, 2002, pp. 2402-2403, vol. 125, Publsiher: American Chemical Society.

Wu et al., "From Pro Defensins to Definsins: Synthesis and Characterization of Human Neutrophil Pro α-Defensin-1 and its Mature Domain," *J. Peptide Res.*, 2003, pp. 53-62, vol. 62.

Wu et al., "Synthesis and Characterization of Human α-Defensins 4-6," *J. Peptide Res.*, 2004, pp. 118-125, vol. 64.

Xiao et al., "A Genome-Wide Screen Identifies a Single β-Defensin Gene Cluster in the Chicken: Implications for the Origin and Evolution of Mammalian Defensins," *BMC Genomics*, Aug. 13, 2004, vol. 5, No. 56, Publisher: BioMed Central.

Xiao et al., "Identification and Functional Characterization of Three Chicken Cathelicidins With Potent Antimicrobial Activity," *Journal of Biological Chemistry*, Feb. 3, 2006, pp. 2858-2867, vol. 281, No. 5, Publisher: The American Society for Biochemistry and Molecular Biology, Inc.

Xiao et al., "Structure-Activity Relationships of Fowlicidin-1, a Cathelicidin Antimicrobial Peptide in Chicken," *FEBS Journal*, 2006, pp. 2581-2593, vol. 273, Publisher: The Authors Journal.

Yang et al., "Multiple Roles of Antimicrobial Defensins, Cathelicidins, and Eosinophil-Derived Neurotoxin in Host Defense," *Annu. Rev. Immunol.*, Jan. 12, 2004, pp. 181-215, vol. 22.

Patil et al., "Rapid Evolution and Diversification of Mammalian α-Defensins as Revealed by Comparative Analysis of Rodent and Primate Genes," *Physiol. Genomics*, Oct. 19, 2004, vol. 20, pp. 1-11, Publisher: The American Physiological Society.

|           | Signal Peptide                            Prosequence                                        |     |
|-----------|---------------------------------------------------------------------------------------------|-----|
| Defa-rs1  | MKTLILLSALVLLALQVQADPIQEAEEETKTEEQPADEDQDVSVSFEGPEASAVQDLRV-                                 |     |
| rDefa6    | MKTLVLLSALVLVAYQVQADPIQGAEEETKTEEQPSDEDQDVSVSFEGPEASALQDFELG                                 |     |
| RatNP4    | MRTLTLLITLLLLALHTQAESPQERAKAAPDQDMVMED-QDIFISFGGYKGTVLQDAVV-                                 |     |
| Cryptdin-4| MKTLVLLSALVLLAFQVQADPIQNTDEETKTEEQPGEEDQAVSISFGGQEGSALHEKSL-                                 |     |
| DEFA5/HD-5| MRTIAILAAILLVALQAQAESLQERADEATTQKQSGEDNQDLAISFAGNGLSALRTSGS-                                 |     |
| CRS1C-1   | MKTLVLLSALALLALQVQADPIQNTDEETKTQEEQPGEEDQAVSVSFGGTEGSALQDVAQR                                |     |
| CRS4C-1   | MKKLVLLFALVLLAFQVQADSIQNTDEETKTEEQPGEKDQAVSVSFGDPQGSALQDAAL-                                 |     |

| Defa-rs1  | RRTLQCSCRR-VCRNTCSCIRLSRSTYAS------------------------------ | 87  |
| rDefa6    | RPVRRCRCRA-NCGPKEYATAFCAQGPFKQFKFCCT------------------------ | 95  |
| RatNP4    | KAGQACYCRIGACVSGERLTGACGLN-GRIYRLCCR------------------------ | 93  |
| Cryptdin-4| -RGLLCYCRKGHCKRGERVRGTCGIR--FLY--CCPRR---------------------- | 92  |
| DEFA5/HD-5| QARATCYCRTGRCATRESLSGVCEIS-GRLYRLCCR------------------------ | 94  |
| CRS1C-1   | RFPWCRKCRVCQKCEVCQKCPVCPTCPQCPKQPLCKERQNKTAITTQAPNTHHKGC     | 116 |
| CRS4C-1   | --GWGRRCPQCPRCPSCPSCPRCPRCPRCK----CNPK---------------------- | 91  |

Figure 1

SEQUENCE LISTING

<160> NUMBER OF SEQ ID NOS: 6

<210> SEQ ID NO 1
<211> LENGTH: 31
<212> TYPE: PRT
<213> ORGANISM: Rattus sp.

<400> SEQUENCE: 1

Leu Arg Val Arg Arg Thr Leu Gln Cys Ser Cys Arg Arg Val Cys Arg
1               5                   10                  15

Asn Thr Cys Ser Cys Ile Arg Leu Ser Arg Ser Thr Tyr Ala Ser
            20                  25                  30

<210> SEQ ID NO 2
<211> LENGTH: 25
<212> TYPE: PRT
<213> ORGANISM: Rattus sp.

```
-continued

<400> SEQUENCE: 2

Leu Gln Cys Ser Cys Arg Arg Val Cys Arg Asn Thr Cys Ser Cys Ile
1               5                   10                  15

Arg Leu Ser Arg Ser Thr Tyr Ala Ser
            20                  25

<210> SEQ ID NO 3
<211> LENGTH: 22
<212> TYPE: PRT
<213> ORGANISM: Rattus sp.

<400> SEQUENCE: 3

Leu Arg Val Arg Arg Thr Leu Gln Cys Ser Cys Arg Arg Val Cys Arg
1               5                   10                  15

Asn Thr Cys Ser Cys Ile
            20

<210> SEQ ID NO 4
<211> LENGTH: 26
<212> TYPE: PRT
<213> ORGANISM: Rattus sp.

<400> SEQUENCE: 4

Leu Arg Val Arg Arg Thr Leu Gln Cys Ser Cys Arg Arg Val Cys Arg
1               5                   10                  15

Asn Thr Cys Ser Cys Ile Arg Leu Ser Arg
            20                  25

<210> SEQ ID NO 5
<211> LENGTH: 16
<212> TYPE: PRT
<213> ORGANISM: Rattus sp.

<400> SEQUENCE: 5

Leu Gln Cys Ser Cys Arg Arg Val Cys Arg Asn Thr Cys Ser Cys Ile
1               5                   10                  15

<210> SEQ ID NO 6
<211> LENGTH: 31
<212> TYPE: PRT
<213> ORGANISM: Artificial
<220> FEATURE:
<223> OTHER INFORMATION: synthetic peptide based on ratussin sequence

<400> SEQUENCE: 6

Leu Arg Val Arg Arg Thr Leu Gln Ala Ser Ala Arg Arg Val Ala Arg
1               5                   10                  15

Asn Thr Ala Ser Ala Ile Arg Leu Ser Arg Ser Thr Tyr Ala Ser
            20                  25                  30
```

ANTI-MICROBIAL DEFENSIN-RELATED PEPTIDES AND METHODS OF USE

CROSS-REFERENCE TO RELATED APPLICATIONS

This application claims benefit of U.S. provisional patent application 60/846,030, filed Sep. 20, 2006, the complete contents of which are herein incorporated by reference.

SEQUENCE LISTING

This application includes as the Sequence Listing the complete contents of the accompanying text file "Sequence.txt", created Sep. 18, 2007, containing 2,063 bytes, hereby incorporated by reference.

DESCRIPTION

Background of the Invention

1. Field of the Invention

The invention generally relates to antimicrobial peptides. In particular, the invention provides a novel defensin-related antimicrobial peptide and its analogs that are insensitive to physiological concentrations of salt and divalent cations.

2. Background of the Invention

The emergence of antibiotic resistant pathogens has become a world-wide health crisis and alternatives to traditional antibiotics are being sought. Antimicrobial peptides, essential components of the innate immune system, are capable of killing a broad spectrum of bacteria through physical interaction and disruption of membranes. This antibacterial property confers on these peptides an equal activity against both antibiotic-resistant and antibiotic-susceptible bacterial strains. Moreover, it is extremely difficult for bacteria to develop resistance to antimicrobial peptides. Therefore, these peptides are actively being explored to treat bacterial infections, particularly those caused by antibiotic-resistant strains.

Unfortunately, a majority of antimicrobial peptides discovered to date show a significantly reduced antibacterial activity in the presence of physiological concentrations of salt and divalent cations. Therefore, the use of these peptides for the treatment of systemic bacterial infections, or for use in applications that require exposure of the peptide to physiological concentrations of salt (e.g. during delivery of the peptide to a site of infection), is limited or ineffectual.

There is an ongoing need to identify and develop agents with antibacterial activity, particularly agents that maintain their bactericidal activity under physiological conditions.

SUMMARY OF THE INVENTION

The present invention is based on the discovery of a novel, non-toxic antimicrobial peptide that maintains activity under physiological salt and divalent cation conditions. A genome-wide computational screen of the entire rat genome led to identification of a peptide precursor related to defensins, which was denominated "Defa-rs1" (Patil et al., Physiol. Genomics, 20:1-11, 2004). However, no functional characterization of Defa-rs1 was provided in that publication. Furthermore, the mechanism by which biologically active, mature peptide is generated from defa-re1 remains unknown, as does the identity of the native, mature peptide.

This invention relates to a short 31-amino acid peptide, synthesized based on the C-terminal region of defa-rs1, which was named rattusin. The selection of the 31-amino acid peptide sequence which was synthesized was arbitrary, and the invention can be practiced with variants of the peptide sequence. Unlike defensins with a canonical six-cysteine motif, rattusin consists of five cysteines with a unique disulfide bonding pattern. Moreover, synthetic rattusin displayed potent, fast-killing activity against a range of Gram-negative and Gram-positive bacteria of clinical and agricultural importance, including antibiotic-resistant strains. Rattusin is thus clearly among the most potent defensins that have been reported. Importantly, rattusin retained its activity in the presence of physiological concentrations of salt and is thus the only defensin-related peptide whose activity is insensitive to salt. In further contrast to known defensins, rattusin also is insensitive to the presence of $Mg^{2+}$. Rattusin therefore represents an attractive drug candidate against systemic, antibiotic-resistant resistant infections.

The invention provides substantially purified peptides having an amino acid sequence represented by a sequence selected from the group consisting of:

LRVRRTLQCSCRRVCRNTCSCIRLSRS TYAS (SEQ ID NO: 1);

LQCSCRRVCRNTCSCIRLSRSTYAS (SEQ ID NO: 2);

LRVRRTLQCSCRRVCRNTCSCI (SEQ ID NO: 3);

LRVRRTLQCSCRRVCRNTCSCIRLSR (SEQ ID NO: 4);

LQCSCRRVCRNTCSCI (SEQ ID NO: 5); and

LRVRRTLQASARRVARNTASAIRLSRSTYAS (SEQ ID NO: 6)

The invention further provides an antibacterial composition that is active under physiological conditions. The composition includes one or more peptides with an amino acid sequence represented by a sequence selected from the group consisting of SEQ ID NO: 1, SEQ ID NO: 2, SEQ ID NO: 3, SEQ ID NO: 4, SEQ ID NO: 5, and SEQ ID NO: 6. In one embodiment of the invention, the salt concentration of the antimicrobial composition is in the range of from 0 to 250 mM salt (and in one embodiment, is at least 50 mM), and the salt is, for example, NaCl or KCl, or both. In another embodiment of the invention, the divalent cation concentration of the antimicrobial composition is in the range of from 0 to 5 mM, (and in one embodiment is at least 1 mM) and the divalent cation is, for example, $Mg^{+2}$ or $Ca^{+2}$, or both.

The invention also provides a method for killing bacteria at a location having a salt concentration in the range of from 0 to 250 mM or a divalent cation concentration in the range of from 0 to 5 mM. The method includes the step of exposing the bacteria to one or more peptides with an amino acid sequence represented by a sequence selected from the group consisting of SEQ ID NO: 1, SEQ ID NO: 2, SEQ ID NO: 3, SEQ ID NO: 4, SEQ ID NO: 5, and SEQ ID NO: 6. The step of exposing kills the bacteria. In one embodiment of the invention, the bacteria are antibiotic-resistant bacteria. In another embodiment of the invention, the location is in vivo. In yet another embodiment, the location is a circulatory, respiratory, digestive, or reproductive system of a patient, and in another embodiment, the location is an open wound.

The invention also provides a method for treating or preventing a bacterial infection in a patient in need thereof. The method includes the steps of 1) providing to the patient a composition containing one or more peptides with an amino acid sequence represented by a sequence selected from the group consisting of SEQ ID NO: 1, SEQ ID NO: 2, SEQ ID NO: 3, SEQ ID NO: 4, SEQ ID NO: 5, and SEQ ID NO: 6, and 2) allowing the peptides to contact bacteria under physiological conditions in order to ameliorate or prevent the bacterial infection. In one embodiment of the invention, provision of the composition is systemic, whereas in another embodiment, provision is topical.

BRIEF DESCRIPTION OF THE DRAWINGS

FIG. 1. Alignment of rat defa-rs1 with representative α-defensins and related sequences. Dashes are created to maximize the alignment. Conserved amino acids are shaded. Rattusin is a 31-amino acid, C-terminal peptide of defa-rs1 as shown underlined. Known mature sequences of other defensins are also underlined. Note the difference in the cysteine pattern between defa-rs1 with other α-defensins, despite a high conservation in the signal and pro-sequences. Abbreviations: rDefa6, rat α-defensin 6; RatNP-4, rat neutrophil protein-4; DEFA5/HD-5, human α-defensin 5; CRS, cryptdin-related sequence.

DETAILED DESCRIPTION OF THE PREFERRED EMBODIMENTS OF THE INVENTION

Figure 2:
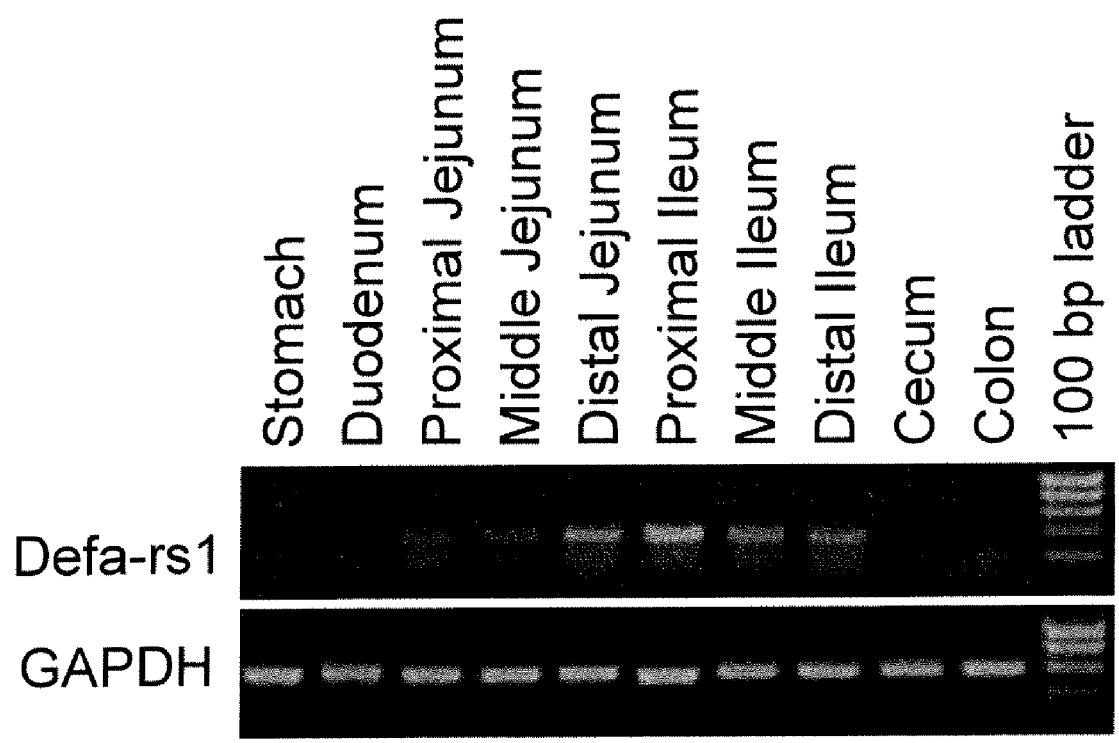
FIG. 2. Expression pattern of defa-rs1/rattusin mRNA in the rat gastrointestinal tract by RT-PCR. The housekeeping gene, GAPDH, was used to normalize template input.

The present invention provides a novel, potent and non-toxic antimicrobial peptide that maintains activity under physiological salt and divalent cation conditions, and analogs thereof. The peptide, referred to herein as "rattusin", is thus suited for use in environments where physiological conditions prevail, e.g. in vivo. This is in contrast to other known defensins which are salt and/or divalent cation sensitive and thus not suitable for use in vivo. The rattusin peptide displayed potent, fast-killing activity against a range of Gram-negative and Gram-positive bacteria of clinical and agricultural importance, including antibiotic-resistant strains. Rattusin is thus clearly among the most potent defensins that have been reported and represents an attractive drug candidate, especially against systemic, antibiotic-resistant infections.

The rattusin peptides and derivatives and conservative variants thereof (i.e. analogs) are salt-insensitive, i.e. they retain their antibacterial activity even in the presence of physiologically relevant concentrations of salt. By "physiologically relevant concentrations of salt" or "physiological salt concentrations" we mean the presence of NaCl or KCl (e.g. in biological fluids) from about 100 to about 200 mM. However, it should be understood that the peptides of the invention are also active at a wider range of salt concentrations e.g. from about 0 to about 250 mM.

In addition, the peptides of the invention also retain their antibacterial activity in the presence of physiologically relevant concentrations of divalent cations (e.g. $Mg^{2+}$ and/or $Ca^{2+}$). By "physiologically relevant concentrations of divalent cations" we mean the presence of $Mg^{2+}$ and/or $Ca^{2+}$ in biological fluids at concentrations ranging from about 1 mM to about 2 mM per divalent cation. However, it should be understood that the peptides of the invention are also active at a wider range of divalent cation concentrations, e.g. from about 0 mM to about 5 mM, per divalent cation.

The primary amino acid sequence of rattusin is LRVR-RTLQCSCRRVCRNTC SCIRLSRSTYAS (SEQ ID NO: 1). However, the amino acid sequence of the antibiotic peptide may be altered somewhat to produce variants, derivatives or analogs that are suitable for use in the present invention. For example, certain conservative amino acid substitutions may be made without having a deleterious effect on the ability of the peptide to function as an antibiotic, without destroying the salt and/or divalent cation tolerance of the peptide, and without increasing toxicity, and in fact may lead to an increase in antibiotic activity and/or a decrease in toxicity. The resulting peptide may be referred to as a "conservative variant" or "conservative derivative" or "conservative analog". Those of skill in the art are familiar with the nature of such conservative substitutions, for example, substitution of a positively charged amino acid for another positively charged amino acid; substitution of a negatively charged amino acid for another negatively charged amino acid; substitution of a hydrophobic amino acid for another hydrophobic amino acid; substitution of an aliphatic amino acid for another aliphatic amino acid; etc. All such substitutions or alterations of the sequence of the peptide of the invention are intended to be encompassed by the present invention, so long as the resulting peptide is still bactericidal and resistant to the effects of physiological salt and/or divalent cation concentrations. In general, such substituted sequences will be at least about 50% identical to the corresponding sequence in SEQ ID NO: 1, preferably about 60 to 70, or even 70 to 80, or 80 to 90% identical to SEQ ID NO: 1, and preferably about 95 to about 100% identical. Those of skill in the art are well-acquainted with the calculation of identity between or among peptide sequences.

In addition, certain other modifications (e.g. chemical modifications) of the peptide are also contemplated. Such modifications may be referred to as variant or derivative or analog forms of the peptide. For example, the carboxyl terminus of the peptide may be amidated; reactive groups may be sulfonylated, lipidated, etc.; or L-amino acids of these sequences may be substituted with D-amino acids. Further, other variations of the sequences disclosed herein may also be carried out, e.g. the addition of a label or tag to the peptide to facilitate the isolation or detection of the peptides; removal or creation of a protease cleavage site; addition of charged or hydrophilic residues to promote solubility of the peptides; addition of specific residues to promote secondary structural elements (e.g. to modulate helicity, amphipathicity, hydrophobicity, or cationicity); etc.

In addition, the amino acid sequences of the peptides of the invention need not contain the precise number of residues as the exemplary optimized peptides disclosed herein. Certain deletions or additions may be tolerated (i.e. deletion or addition analogs), so long as the resulting peptide is bactericidal, of sufficiently low toxicity, and retains its insensitivity to physiological concentrations of salt and/or divalent cations. Especially, additions of other amino acid sequences at either the amino or carboxyl terminal (or both) are also encompassed herein, so long as such additions do not interfere with the activity and attributes of the rattusin peptide. Further, certain non-conservative amino acid substitutions may also be tolerated without compromising the efficacy or attributes of the peptide. Such non-conservative variants (analogs, derivatives) of rattusin will, in general, be at least about 50% identical to SEQ ID NO: 1, preferably about 60 to 70, or even 70 to 80, or 80 to 90% identical to SEQ ID NO: 1, and also preferably about 95 to about 100% identical. Those of skill in the art are well-acquainted with the calculation of identity between or among peptide sequences.

Further, even if the efficacy and/or attributes of rattusin are compromised or diminished somewhat in its analogs, they may still be useful. For example, a peptide that is less potent as an antibiotic may still be of much value if it has superior solubility or stability characteristics, or is less costly to manufacture, when compared to the parent molecule. In general, however, the antibiotic potency and/or divalent cation insensitivity of the analog peptides will be at least about 50%, or preferably about 60%, or more preferably about 70-80%, and most preferably about 90% or more of that of the parent rattusin molecule.

Chimeric polypeptides that contain more than one (i.e. multiple or a plurality of) antibiotic peptide sequence (or variant, analog or derivative) within a polypeptide are also envisioned. The multiple peptides may be in tandem within a single, linear polypeptide chain, and may be separated, for example, by spacer peptides, many examples of which are known in the art. Alternatively, the structure of such a chimera may be branched, or a combination of linear and branched. The peptides that make up the chimera may be the same or different. Further, the chimera may be designed so that it is cleaved by proteases in vivo, releasing individual rattusin peptides.

The peptide of the invention is "antimicrobial" or "antibiotic" or "bactericidal". By "antimicrobial" or "antibiotic" or "bactericidal" we mean that the peptides exhibit a minimum inhibitory concentration in the low micromolar concentration range (<10 μM) when measured by standard broth microdilution assay as recommended by the Clinical and Laboratory Standards Institute (CLSI). In addition, the peptides are non-toxic or of low toxicity. By "non-toxic" and/or of "low toxicity", we mean that lysis of 50% of erythrocytes or killing of 50% mammalian cells occurs at a concentration of >100 μM peptide. Those of skill in the art will recognize that as long as the concentration of peptide that is required in order to be bactericidal is below the level of peptide that is toxic, the peptides may be useful as bactericides.

The antimicrobial peptides of the invention may be used in a variety of ways. For example, they may be used as bactericidal agents to kill or damage unwanted bacteria. Suitable scenarios for such a use of the antimicrobial peptides include but are not limited to: treatment of established bacterial infections (for example, in bacterial hosts or potential bacterial hosts such as humans, other mammals, or any other living or non-living entity that is susceptible to bacterial infection or colonization); or prophylactically for the prevention of bacterial infections in such hosts (e.g. the antimicrobial peptides may be administered to individuals whose immune systems are compromised and who may be susceptible bacterial infections); or administered topically to areas of a host that are susceptible to infection, e.g. to areas of the body that are likely sites for bacterial growth, e.g. the gums, open wounds, vaginal and groin area, bed sores or areas which are likely to develop into bedsores, areas which are likely to be moist, e.g. under dressings, diapers, etc.); and the like. In particular, rattusin may be administered during treatment of a patient in conjunction with other antibiotics e.g. in order to prevent opportunistic infections caused by the overgrowth of normal or opportunistic flora that are not killed by the antibiotic, and/or to prevent the development of bacteria that are resistant to the antibiotic. Alternatively, rattusin may be administered instead of other antibiotics. Ratussin or its analogs may also be included in food preparations that might otherwise be susceptible to bacterial colonization, e.g. preserved goods that are susceptible to *Clostridium botulinum*.

A wide variety of bacterial infections may be treated or prevented by administration of the antimicrobial peptide of the present invention. Examples of such bacteria include but are not limited to: coliform bacteria such as *Escherichia coli; Salmonella* species, e.g. *S. typhimurium, S. enteritidis*, and *S. choleraesuis; Klebsiella* species, e.g. *K. pneumoniae, Pseudomonas* species, e.g. *P. aeruginosa; Listeria* species e.g. *L. monocytogenes; Staphylococcus* species e.g. *S. aureus, Mycobacterium* species e.g. *M. tuberculosis Enterococcus* species, e.g. *E. faecalis; Campylobacter* species, e.g. *C. jejuni, C. coli,* and *C. fetus*; and *Clostridium* species, e.g. *C. perfringens, C. difficile, C. tetani,* and *C. botulinum* In particular, the peptides of the invention may be used to combat bacteria that are resistant to conventional antibiotics, such as MRSA (methicillin-resistant *Staphylococcus aureus*), VRSA (Vancomycin-resistant *S. aureus*), VRE (Vancomycin-Resistant *Enterococcus*), Penicillin-Resistant *Enterococcus,* PRSP (Penicillin-resistant *Streptococcus pneumoniae*), isoniazid/rifampin-resistant *Mycobacterium tuberculosis* and other antibiotic-resistant strains of *E. coli, Salmonella, Campylobacter,* and *Streptococci*. Such bacteria are herein referred to as "antibiotic-resistant" or "drug-resistant" or "multidrug-resistant", or by other similar terms that are well understood in the art.

Several diseases or disease conditions that are associated with bacterial infections may be treated with the antibiotic peptides of the invention. Examples of such diseases or conditions include but are not limited to sepsis, pneumonia, cystic fibrosis-associated chronic respiratory infections, inflammatory bowel diseases (particularly Crohn's disease), acne, and catheter-related infections, and others. In addition, the antibiotic peptides of the invention may be administered prophylactically to patients who are at risk for developing bacterial infections, e.g. those with compromised immune systems due to, for example, HIV infection, chemotherapy, etc., and those who have been treated with a course of traditional antibiotics.

The present invention also provides new compositions for use in administration to patients (generally humans or mammals). The compositions include a substantially purified antimicrobial peptide as described herein, and a physiologically compatible carrier. In one embodiment of the invention, the composition in which the microbial peptide is contained comprises physiological levels of salt or divalent cations, or both. In other words, the salt concentration in the composition is in the range of 0-250 mM, and preferably is about 100 mM; and/or the divalent cation concentration in the composition is in the range of from about 0 mM to about 5 mM, and preferably is about 1 mM. Examples of salts that may be used in the preparation of such compositions include but are not limited to NaCl and KCl. Examples of sources of divalent cations include but are not limited to $MgCl_2$, $MgSO_4$, $CaCl_2$, $MgSO_4$, $MnCl_2$, and $MnSO_4$, etc. In some embodiments, the only antimicrobial agent in the composition is the microbial peptide of the present invention. However, in other embodiments other antimicrobial agents may also be present, i.e. a "cocktail" or mixture of two or more different antimicrobial agents (e.g. other antimicrobial peptides or traditional antibiotics) may be administered.

The preparation of compositions for use as antimicrobial agents is well known to those of skill in the art. Typically, such compositions are prepared either as liquid solutions or suspensions; however solid forms such as tablets, pills, powders, pastes, ointments, suppositories, gelatinous compositions, and the like are also contemplated, as are aerosol forms. Solid forms suitable for solution in, or suspension in, liquids prior to administration may also be prepared. The preparation may also be emulsified, or incorporated into nanoparticles, microparticles, biodegradable polymers such as polylactide (PLA) and its copolymers with glycolide (PLGA), etc. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of antimicrobial peptide in the formulations may vary. However, in general, the amount in the formulations will be from about 1-99%, weight/volume.

The antimicrobial peptide compositions (preparations) of the present invention may be administered by any of the many suitable means which are well known to those of skill in the art, including but not limited to by injection, inhalation, orally, intravaginally, intranasally, by ingestion of a food or probiotic product containing the antimicrobial peptide, topically, as eye drops, via sprays, incorporated into dressings or bandages (e.g. lyophilized forms may be included directly in the dressing), etc. In preferred embodiments, the mode of administration is topical or orally or by injection. In addition, the compositions may be administered in conjunction with other treatment modalities such as substances that boost the immune system, various chemotherapeutic agents, other antibiotic agents, and the like.

The present invention also provides a method of killing or damaging bacteria, particularly in environments where physiological concentrations of salt and/or divalent cations prevail. In such environments, which include most in vivo applications, other antimicrobial peptides cannot be used because their antibacterial activity is destroyed by the salt and/or divalent cations that are normally present in vivo. As described above, the antimicrobial peptide of the present invention does not suffer from such limitations. The method involves contacting the bacteria with the antimicrobial peptides of the invention. In some instances, the bacteria will be killed outright, and signs or symptoms of bacterial colonization or infection will be completely eradicated. However, those of skill in the art will recognize that much benefit can be derived even if all bacteria in a population are not killed outright. For example, in some cases, the ability of the bacteria to carry out metabolic reactions may be slowed or otherwise attenuated by exposure to the antimicrobial peptides, or the reproductive potential of the bacteria may be decreased. All such lessening of the bacteria's ability to flourish in an environment in which they would typically establish colonies and persist may be of benefit to a host organism in need of treatment with the antimicrobial peptides of the invention.

While in one embodiment of the invention, treatment of bacterial host organisms or potential bacterial host organisms is contemplated (e.g. humans and other mammals, so that veterinary uses are also included), other uses of the antimicrobial peptides of the invention will also occur to those of skill in the art. For example, the treatment of surfaces for food preparation or of edible substances that might otherwise become colonized by bacteria; use in cleansing products such as soaps, detergents, lotions, etc.; for sterilization of drinking water; in packaging material; etc.

EXAMPLES

Example 1

Characterization of Rattusin

The emergence of antibiotic-resistant pathogens has become a major health crisis worldwide (1, 2). Novel antimicrobial drugs against resistant microbes are urgently needed. Defensins, an essential component of the innate immune system, are capable of killing a broad spectrum of bacteria through membrane permeabilization. These peptides initially interact with negatively charged phospholipids through electrostatic interaction leading to subsequent cell membrane depolarization and disruption leading to cell death (3, 4). The physical mechanism of action ensures that they act on a broad spectrum of bacteria (including antibiotic-resistant strains), with an extremely low risk of developing resistance by bacteria. Therefore, defensins represent attractive antibacterial drug candidates particularly against resistant bacteria.

Defensins are ubiquitously present in plants, fungi, insects, and vertebrate animals, including humans (3-8). In vertebrates, defensins are characterized by the presence of multiple cysteines in well-defined spacing patterns. Based on the number and spacing pattern of cysteines, vertebrate defensins are further divided into six subfamilies. Besides well-described α-, β-, and θ-defensins with six characteristic cysteines (3, 4, 8-11), two groups of mouse-specific a-defensinrelated sequences (CRS1C and CRS4C) exist with 9 or 11 cysteines (12-14). While β-defensins are preferentially expressed in mucosal epithelial cells lining mucosal surfaces of the reproductive, digestive, and respiratory tracts, most α- and θ-defensins as well as mouse CRS1C and CRS4C are produced in the granules of either phagocytes or Paneth cells, which are specialized cells lining the bottom of intestinal crypts (3, 4, 8-11).

All defensins are strategically synthesized in precursor forms, and proteolytic processing is required to generate biologically active, mature peptides. Proteases responsible for the cleavage and activation of defensins have been identified in several cases. Trypsin is specifically involved in the proteolysis of human defensin-5 (DEFA5/HD5) following an arginine residue (15), while matrix metalloproteinase 7 (MMP-7 or matrilysin) prefers to cleave enteric mouse a-defensins, known as cryptdins, after the serine residue (16, 17).

Besides having direct microbicidal activities, AMPs have increasingly been appreciated to play a profound role in regulating host immune responses to infections. Many peptides are shown to be actively involved in chemotaxis and activation of immune cells, regulation of dendritic cell differentiation, induction of angiogenesis and re-epithelialization, and modulation of cytokine and chemokine gene expression (18-20). However, the potential of defensins as therapeutics is dampened by a loss of the activity in the presence of physiological concentrations of NaCl or divalent cations (such as $Mg^{2+}$ and $Ca^{2+}$) (3, 8). Consequently, none of the defensin-based therapeutics, except for a fungal defensin, plectasin (21), are under clinical development.

We recently discovered a defensin-related peptide precursor, namely defa-rs1, through a comprehensive genome-wide computational screen of the rat genome (22). Unlike defensins with a canonical six-cysteine motif, defa-rs1 consists of five cysteines with a unique disulfide bonding pattern (FIG. 1). However, neither the mechanism by which biologically active, mature peptide is generated from defa-rs1, nor the identity of the native, mature peptide is known.

The following Example describes the synthesis and characterization of a 31 amino acid peptide, the sequence of which was selected arbitrarily based on the C-terminal region of defa-rs1. Functional analyses of the peptide (denominated rattusin) show that rattusin possesses potent antibacterial activity against Gram-positive and Gram-negative bacteria including antibiotic-resistant bacteria. More importantly, rattusin retains the antibacterial activity in serum or in the presence of high concentrations of salt and divalent cations. These properties make rattusin an attractive candidate for further therapeutic development. However, those of skill in the art will recognize that the sequence of rattusin is exemplary in nature, and that variants of this sequence may also be used in the practice of the invention.

MATERIALS AND METHODS

RT-PCR Analysis of the Gene Expression Pattern of defa-rs1/Rattusin

Different sequential segments of gastrointestinal tracts from stomach to colon were collected from 2 month old Sprague-Dawley rats. Total RNA was extracted using TRIzol (Invitrogen, Carlsbad, Calif.). For each gastrointestinal segment RNA, 4 µg were reverse transcribed using random hexamers and SuperScript II reverse transcriptase and a first-strand cDNA synthesis kit (Invitrogen, Carlsbad, Calif.) according to manufacturer's instruction. The subsequent PCR was carried out as described (22). Briefly, 1/40th of the first-strand cDNA was used to amplify defa-rs1/rattusin and glyceraldehyde-3-phosphate dehydrogenase (GAPDH) with gene specific primers. The PCR product was analyzed by electrophoresis on 1.2% agarose gel containing 0.5 µg/ml ethidium bromide. The identity of rattusin PCR product was confirmed by cloning into a pGEM-T Easy vector (Promega, Madison, Wis.) followed by direct sequencing of a recombinant plasmid.

Peptide Synthesis

Rattusin of 31 amino acids (LRVRRTLQCSCRRVCRNTCSCIRLSRSTYAS, SEQ ID NO: 1) was obtained from Bio-synthesis (Lewisville, Tex.), having been chemically synthesized in the reduced form using standard solid-phase synthesis and purified by reverse phase-high pressure liquid chromatography (RP-HPLC) to >95% purity. The mass of the peptide was confirmed by matrix assisted laser desorption ionization-time of flight (MALDI-TOF) mass spectrometry (MS) using Voyager DE-PRO (Applied Biosystems, Foster City, Calif.) housed in the recombinant DNA/protein core facility at Oklahoma State University. Recombinant cryptdin 4, the most potent α-defensin in the mouse, was produced in bacteria as described (23, 24). HD-5 was chemically synthesized as described (25). Cryptdin-4 and HD-5 were used as the reference peptides.

Refolding of Synthetic Rattusin

Synthetic rattusin in the reduced form at 0.1 mg/ml was exposed to $O_2$ gas for 5 min in 50 mM Tris, pH 8.0, and stirred for 48 h at room temperature with the cap open as described (14). Following air oxidation, refolded rattusin was purified by RP-HPLC on a 4.6×250 mm Vydac C18 column (Grace Vydac, Hesperia, Calif.) and BioLogic Duo Flow liquid chromatography system (Biorad, Hercules, Calif.). Buffer A consisted of 5% acetonitrile & 0.18% trifluoroacetic acid (TFA) and Buffer B consisted of 90% acetonitrile & 0.15% TFA. The gradient used was 0 to 60% buffer B over 90 minutes at a flow rate of 1 ml/min. The eluted peptide was lyophilized and stored at −80° C. until use.

Bacterial Culture and Antibacterial Assays

All bacterial strains were purchased from either MicroBiologics (St. Cloud, Minn.) or ATCC (Manassas, Va.). Bacteria were grown in trypticase soy broth (TSB) overnight and subcultured in the same broth for 3-4 h at 37° C. in a shaking incubator to the mid log phase. To study the antibacterial spectrum, a modified broth microdilution assay was used as described (26). Briefly, the mid log phase bacteria were washed with 25 mM sodium phosphate buffer, pH 7.4, and suspended in 5% TSB in 25 mM sodium phosphate, pH 7.4, to 5×10⁵ CFU/ml with and without 100 mM NaCl. Bacteria (90 µl) were then dispensed in a 96-well plate, followed by addition of peptides (10 µl) serially diluted in 0.01% acetic acid. After overnight incubation at 37° C., the minimum inhibitory concentration (MIC) of each peptide was determined as the lowest concentration that gave no visible bacterial growth.

To study the kinetics of bacterial killing, a standard colony counting assay was used as described (26). Rattusin and cryptin-4 were incubated with 90 µl of 5×10⁵ CFU/ml *Staphylococcus aureus* ATCC 25923 at the concentration of 2 µM each or with *E. coli* O157:H7 at the concentration of 4 µM each in 25 mM sodium phosphate buffer, pH 7.4, with and without 100 mM NaCl. The reaction was incubated at 37° C. for 10, 30, 60, 120 and 240 min and diluted rapidly with ice-cold PBS and plated immediately. Plates were incubated at 37° C. for 14-18 hours and viable bacteria were counted.

The effect of $Mg^{2+}$ on the antibacterial activity was studied by incubating rattusin and cryptdin-4 for 4 h with 90 µl of $5 \times 10^5$ CFU/ml *Staphylococcus aureus* at a concentration of 2 µM each or with *E. coli* O157:H7 at a concentration of 4 µM each in 1% TSB, 25 mM sodium phosphate buffer, containing 0, 1, 2 and 5 mM of $MgCl_2$, pH 7.4.

Cytotoxicity Assay

Cytotoxicity against human Caucasian colon adenocarcinoma (CACO-2) cell line (ATCC, Manassas, Va.) was measured using alamarBlue dye (Biosource, Camarillo, Calif.) as described previously (26, 27). Briefly, CACO-2 cells were seeded into 96 well plate at $5 \times 10^4$ in Dulbecco's modified Eagle's medium (DMEM) with 10% FBS and were grown overnight. The next day cells were washed once with DMEM followed by the addition of fresh DMEM with and without 10% FBS and 100 µM of rattusin or cryptdin-4 or fowlicidin-1. After 18 hours of incubation, alamarBlue at 10% final amount was added to cells and cells were further incubated for 6 hours at 37° C. in a humidified 5% $CO_2$ incubator. The plate was read with excitation at 545 nm and emission at 590 nm. The percentage of cell death was calculated as $[1-(F_{peptide}-F_{background})/(F_{acetic\ acid}-F_{background})] \times 100$, where $F_{peptide}$ is the fluorescence of cells exposed to 100 µM peptide, $F_{acetic\ acid}$ is the fluorescence of cells exposed to 0.01% acetic acid only, and $F_{background}$ is the background fluorescence of 10% alamarBlue dye in cell culture medium without cells.

Results

Identification of Rattusin, a Novel Defensin-related Peptide

The complete repertoires of the α-, β-, and θ-defensin gene families in a range of animal species have been identified by employing a comprehensive computational strategy (22, 28, 29). Among over 100 novel defensins identified is a unique sequence in the rat, denominated "defa-rs1" (22). Defa-rs1 shares a significant similarity with α-defensins in the signal and pro-sequences (22) (FIG. 1). However, unlike any classical α-defensins or mouse defensin-related peptides, defa-rs1 has five cysteines with a different spacing pattern in the C-terminal region (FIG. 1).

To further analyze the detailed expression pattern of the Defa-rs1 gene, various intestinal segments were harvested across the longitudinal axis of 2-month old healthy rats, extracted for RNA, and subjected to RT-PCR analysis of Defa-rs1 mRNA expression levels. As shown in FIG. 2, Defa-rs1 mRNA was highly expressed in distal jejunum and the entire ileum, but not in other parts of the gastrointestinal tract. Cryptdin-4 and HD-5, Paneth cell-specific α-defensins, also show a similar expression pattern in small intestine (30-32). This suggests that, similar to enteric α-defensins, Defa-rs1 is likely to be produced by Paneth cells.

Antibacterial Properties of Rattusin

Figure 3:
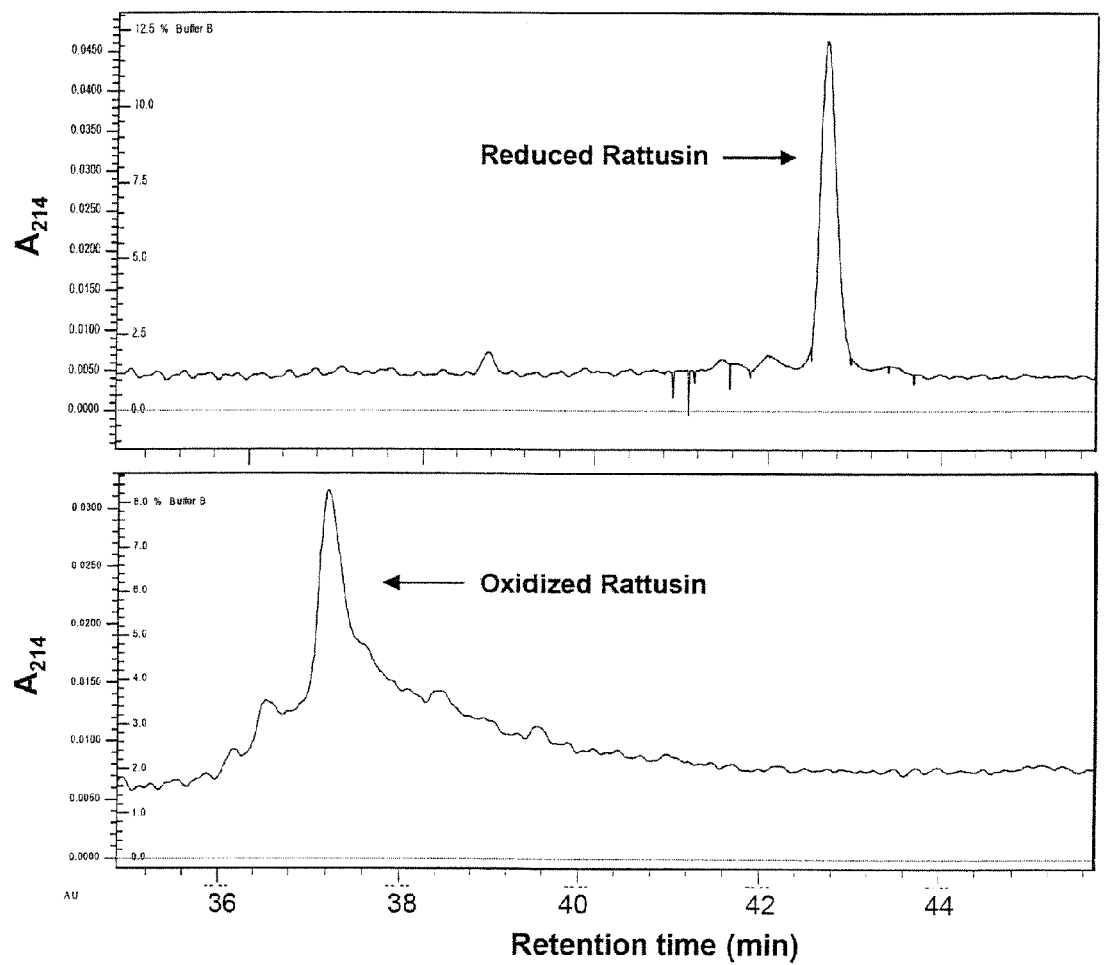
FIG. 3. RP-HPLC profiles of reduced and oxidized rattusin. Reduced synthetic peptide was refolded by air oxidation in 50 mM Tris buffer, pH 8.0, for 48 h. Oxidized rattusin was purified to homogeneity by RP-HPLC. Note that there is a decrease in the retention time of oxidized rattusin due to refolding.

To test whether defa-rs1 is a putative defensin precursor and whether its carboxyl-terminal region is antibacterially active, we synthesized a 31-amino acid peptide containing 5 cysteines, the sequence of which was selected based on the defa-rs1 sequence. (The selection of the amino terminus of the peptide was arbitrary, in that the pattern of in vivo processing of defa-rs1 is unknown. Thus, other similar variant sequences may also display similar desirable characteristics.) This selected peptide was named rattusin (short for "rattus defensin"). Rattusin was synthesized in the reduced form and then further oxidized. Successful refolding was confirmed by RP-HPLC, showing a decrease in the retention time due to the formation of disulfide bonds and a change in the conformation (14, 33, 34) (FIG. 3).

Refolded rattusin was then used to study its antibacterial activity against representative Gram-positive and Gram-negative bacteria by a modified broth microdilution assay with and without 100 mM NaCl. As shown in Table 1, rattusin exhibited a broad spectrum of antibacterial activity with the MIC value in the range of 2-4 µM against most bacterial strains tested. Rattusin was slightly more potent than the most potent mouse Paneth cell α-defensin, cryptdin 4 (9) in most cases. Furthermore, the antibacterial activity of rattusin remained largely unchanged in the presence of 100 mM NaCl, in sharp contrast to cryptdin-4, whose activity was dramatically diminished by salt. Importantly, rattusin also displayed a similar antibacterial efficiency against two strains of methicillin-resistant *Staphylococcus aureus* (MRSA) and multi-drug resistant *Salmonella typhimurium* DT 104 (Table 1).

TABLE 1

Antibacterial spectrum of rattusin

| | | MIC (µM) | | | |
| | | Rattusin | | Cryptidin-4 | |
| Bacteria | ATCC Number | 0 mM NaCl | 100 mM NaCl | 0 mM NaCl | 100 mM NaCl |
| --- | --- | --- | --- | --- | --- |
| Gram-negative | | | | | |
| *E. coli* O157:H7 | 700728 | 2-4 | 2 | 8-16 | >16 |
| *S. typhimurium* | 14028 | 4 | 8 | 8 | >16 |
| *S. typhimurium* DT104 | 700408 | 4 | 4-8 | 4-8 | >16 |
| *K. pneumoniae* | 13883 | 2-4 | 4-8 | 8 | >16 |
| Gram-positive | | | | | |
| *S. aureus* | 25923 | 4 | 4 | 4-8 | ≧16 |
| *L. monocytogenes* | 19115 | 4 | 4 | 8 | >16 |
| *S. aureus* (MRSA) | 43300 | 4 | 4 | 2 | 8 |
| *S. aureus* (MRSA) | BAA-39 | 4-8 | 4-8 | 1 | >16 |

Figure 4:
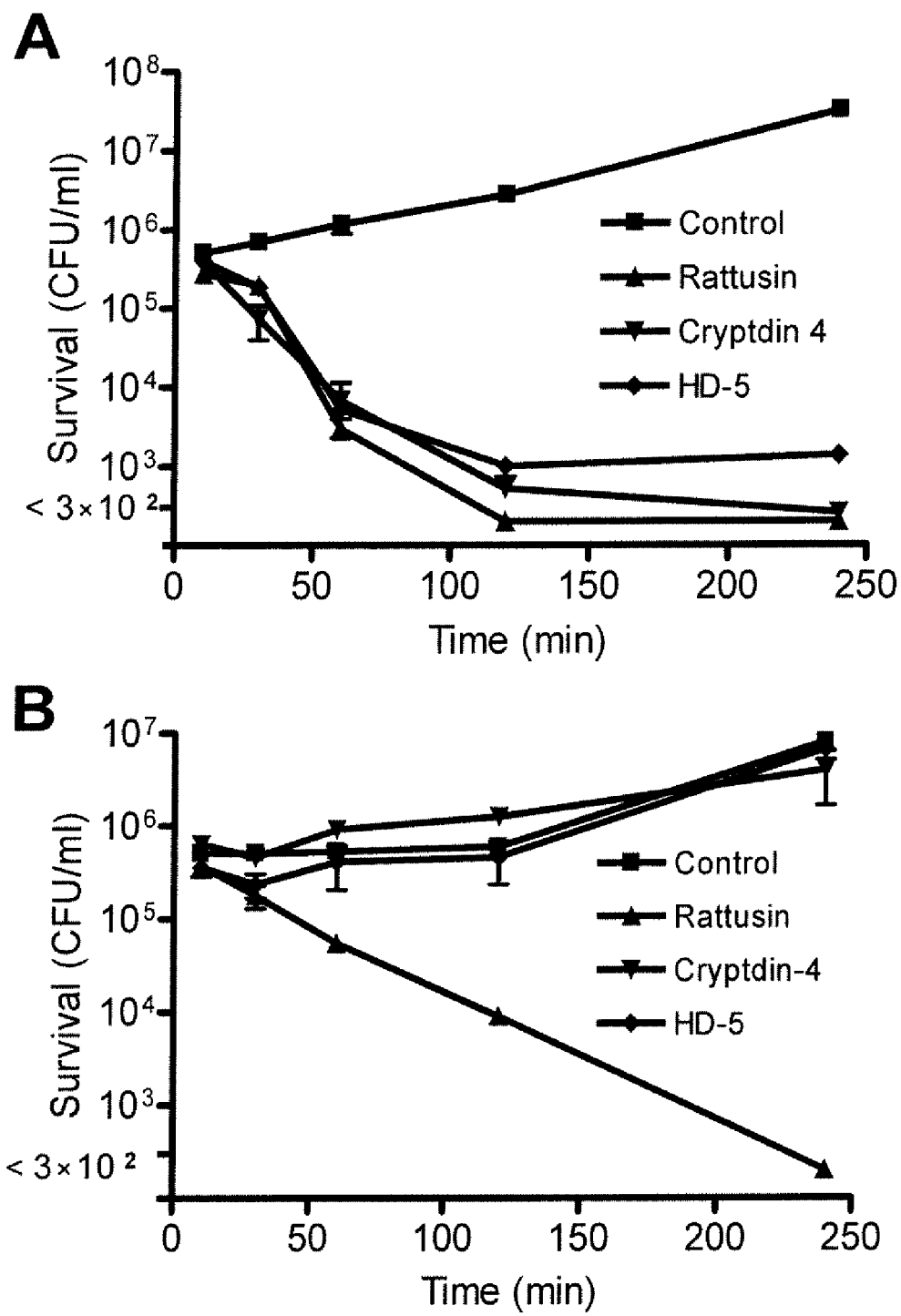
FIG. 4. Kinetics of killing of E. coli O157:H7 in the absence (A) and presence (B) of 100 mM NaCl by rattusin, cryptdin-4 and HD-5. E. coli O157:H7 ATCC 700728 was incubated with 4 µM rattusin, cryptdin-4, HD-5, or an equal volume of 0.01% acetic acid (no peptide) in duplicate in 25 mM sodium phosphate buffer, pH 7.4, 1% TSB with and without 100 mM NaCl for 10, 30, 60, 120 and 240 min. Surviving bacteria were plated and counted. Data shown are means ± SEM of two independent experiments.
Figure 5:
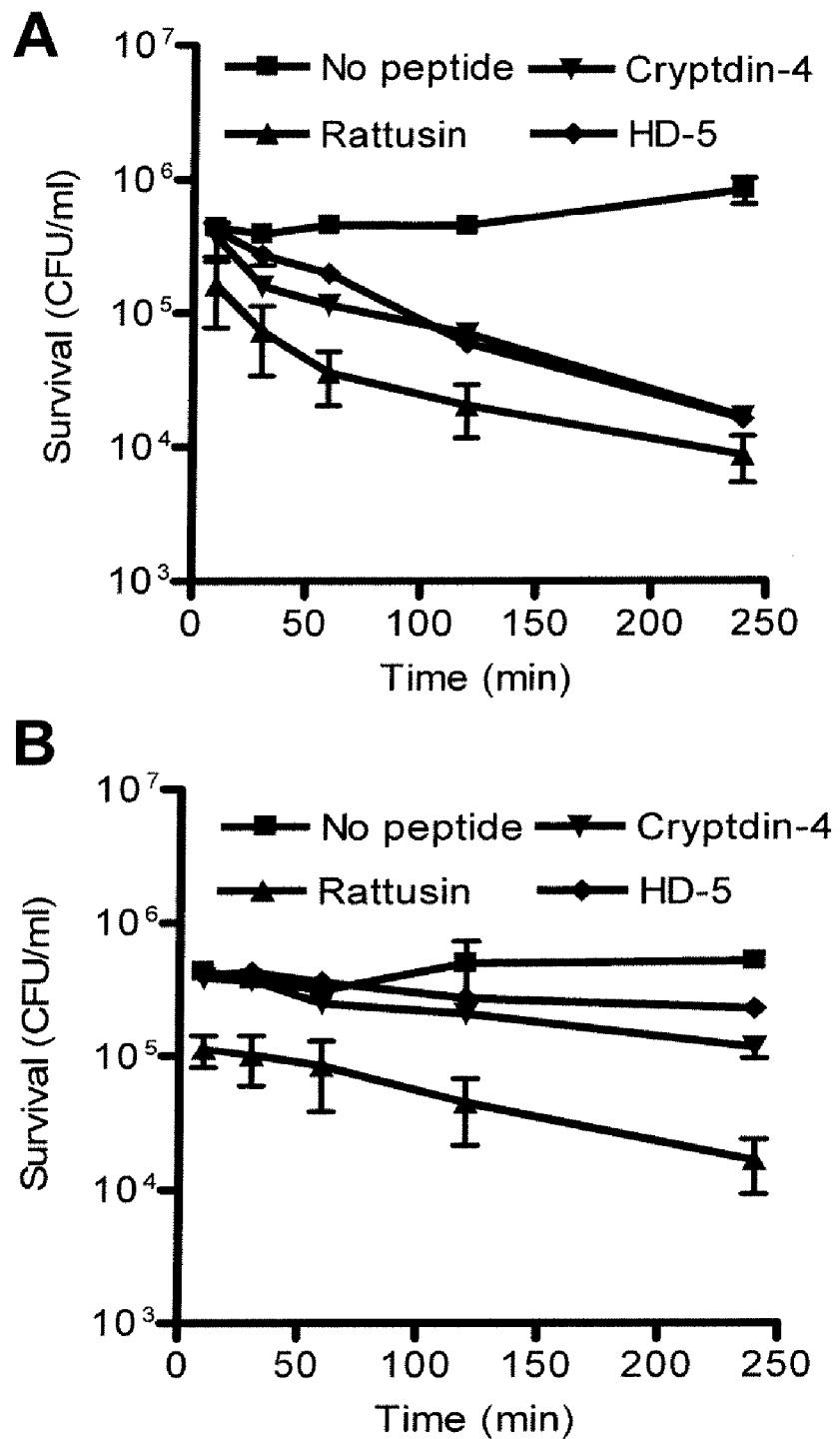
FIG. 5. Kinetics of killing of S. aureus in the absence (A) and presence (B) of 100 mM NaCl by rattusin, cryptdin-4 and HD-5. S. aureus ATCC 25923 was incubated with 2 µM rattusin, cryptdin-4, HD-5, or an equal volume of 0.01% acetic acid (no peptide) in duplicate in 25 mM sodium phosphate buffer, pH 7.4, 1% TSB with and without 100 mM NaCl for 10, 30, 60, 120 and 240 min. Surviving bacteria were plated and counted. Data shown are means ± SEM of two independent experiments.
Figure 6:
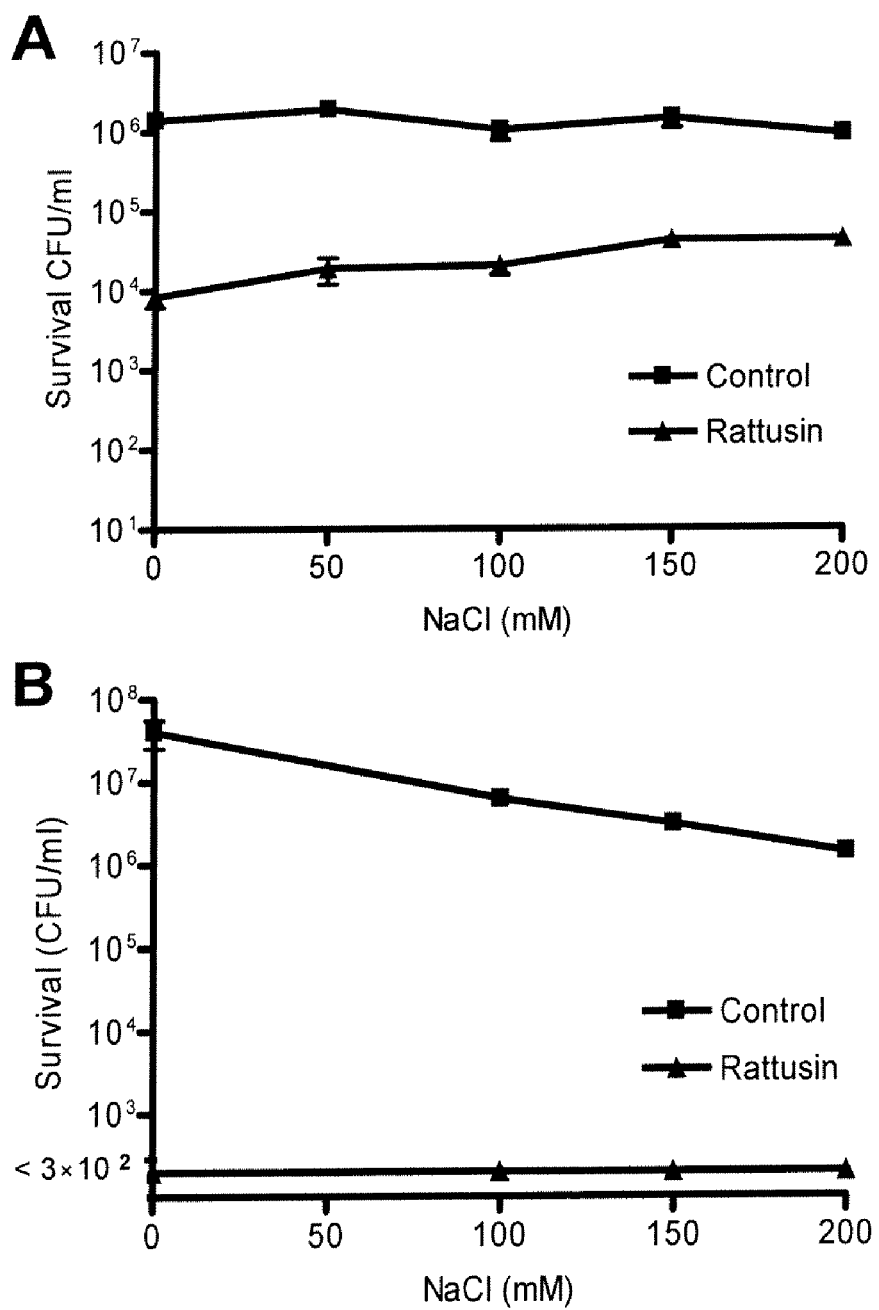
FIG. 6. Effect of salinity on the antibacterial activity of rattusin against S. aureus (A) and E. coli O157:H7 (B). S. aureus and E. coli were incubated with 2 and 4 µM of rattusin, or an equal volume of 0.01% acetic acid (no peptide) in 25 mM sodium phosphate buffer, pH 7.4, 1% TSB with increasing concentrations of NaCl, for 4 h. Surviving bacteria were plated and counted. Data shown are means ± SEM of two independent experiments.

To study the kinetics of bacterial killing, one representative strain of Gram-negative and Gram-positive bacteria was used in a standard colony counting assay. Rattusin, cryptdin-4 and HD-5 at 4 µM killed *E. coli* by three logs within 2 h (FIG. 4A). In the presence of 100 mM NaCl, killing of bacteria by rattusin was slightly delayed with a complete killing occurring at 4 h. In contrast, Cryptdin-4 and HD-5 were completely inactivated in 100 mM NaCl (FIG. 4B). A similar trend also occurred with *S. aureus*. All three peptides at 2 µM killed *S. aureus* by two logs in 4 h (FIG. 5A). Killing of *S. aureus* by rattusin was largely unaffected by 100 mM NaCl, whereas cryptdin-4 and HD-5 were significantly inhibited in the presence of salt (FIG. 5B). Collectively, these results clearly suggested that rattusin with a broad-spectrum, salt-insensitive bactericidal activity is among the most potent defensins. To further study the effect of salinity, the antibacterial activity of rattusin was examined in the presence of increasing concentrations of NaCl. As shown in FIG. 6, rattusin maintained antibacterial activity against both *E. coli* and *S. aureus* in up to 200 mM NaCl.

Figure 7:
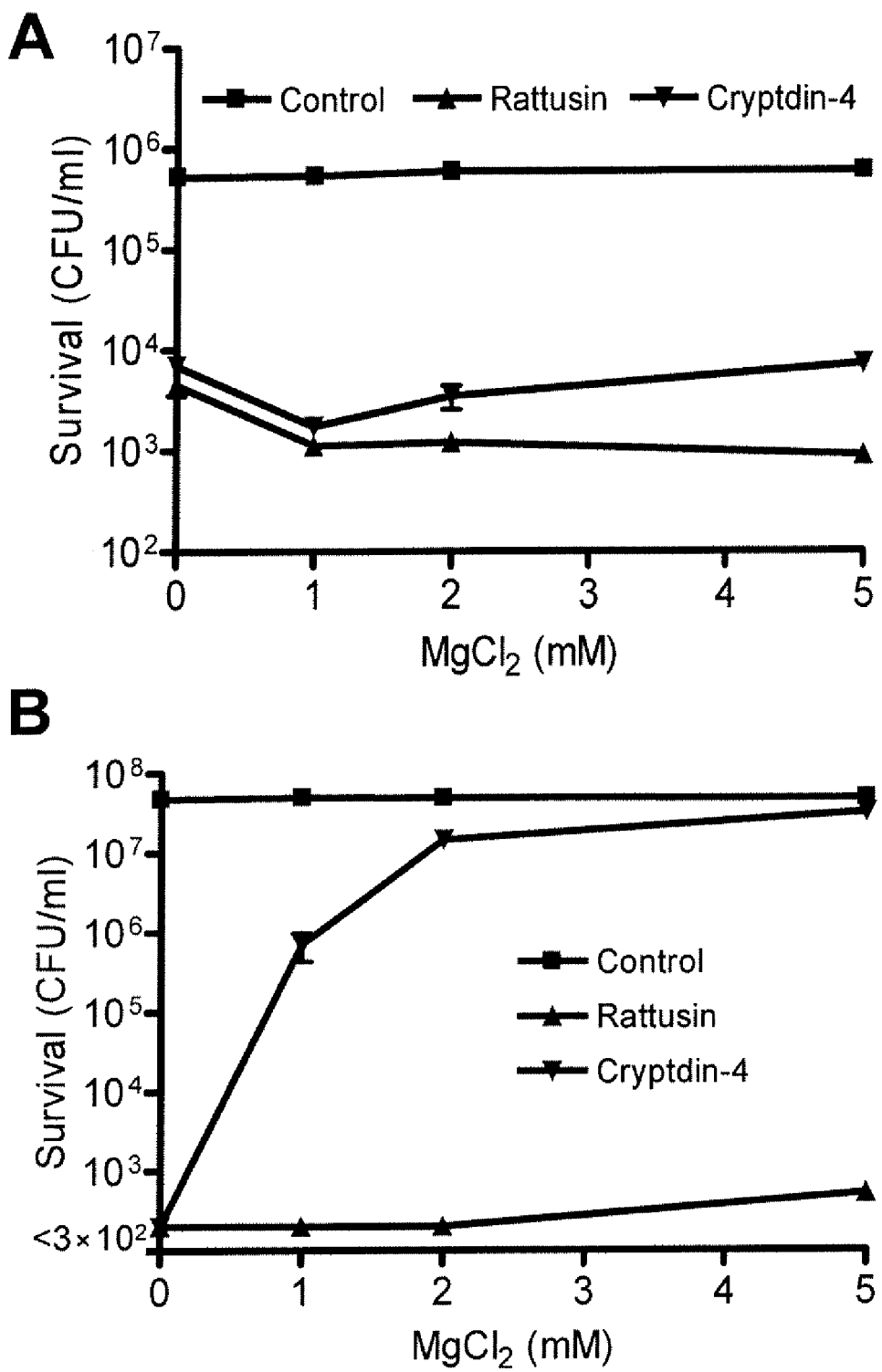
FIG. 7. Effect of $Mg^{2+}$ on the antibacterial activity of rattusin and cryptdin-4 against S. aureus (A) and E. coli O157:H7 (B). S. aureus or E. coli were incubated with rattusin, cryptdin-4, or an equal volume of 0.01% acetic acid (no peptide) in 25 mM sodium phosphate buffer, containing 1% TSB with 0, 1, 2 and 5 mM $MgCl_2$, pH 7.4, for 4 h. Surviving bacteria were plated and counted. Both peptides were used at identical concentrations for each bacterial strain (2 and 4 µM against S. aureus and E. coli, respectively). Data shown are means ± SEM of 2-3 independent experiments.

Divalent cations such as $Mg^{2+}$ are usually present at 1 to 2 mM in most biological fluids (20, 35). At such low concentrations, divalent cations are known to inhibit antibacterial activities of cationic peptides (36, 37). To study the effect of $Mg^{2+}$ on the antibacterial activity, rattusin and cryptdin-4 were incubated with bacteria in the presence of increasing concentrations of $MgCl_2$. There was a dose-dependent loss of the activity of cryptdin-4 against *E. coli* with complete inactivation occurring at 2-5 mM of $MgCl_2$ (FIG. 7A). In contrast, the activity of rattusin was largely unaffected in the presence of $MgCl_2$ (FIG. 7A). $Mg^{2+}$ did not inhibit the activity of either rattusin or cryptdin-4 against *S. aureus* (FIG. 7B).

No Cytotoxicity of Rattusin

Figure 8:
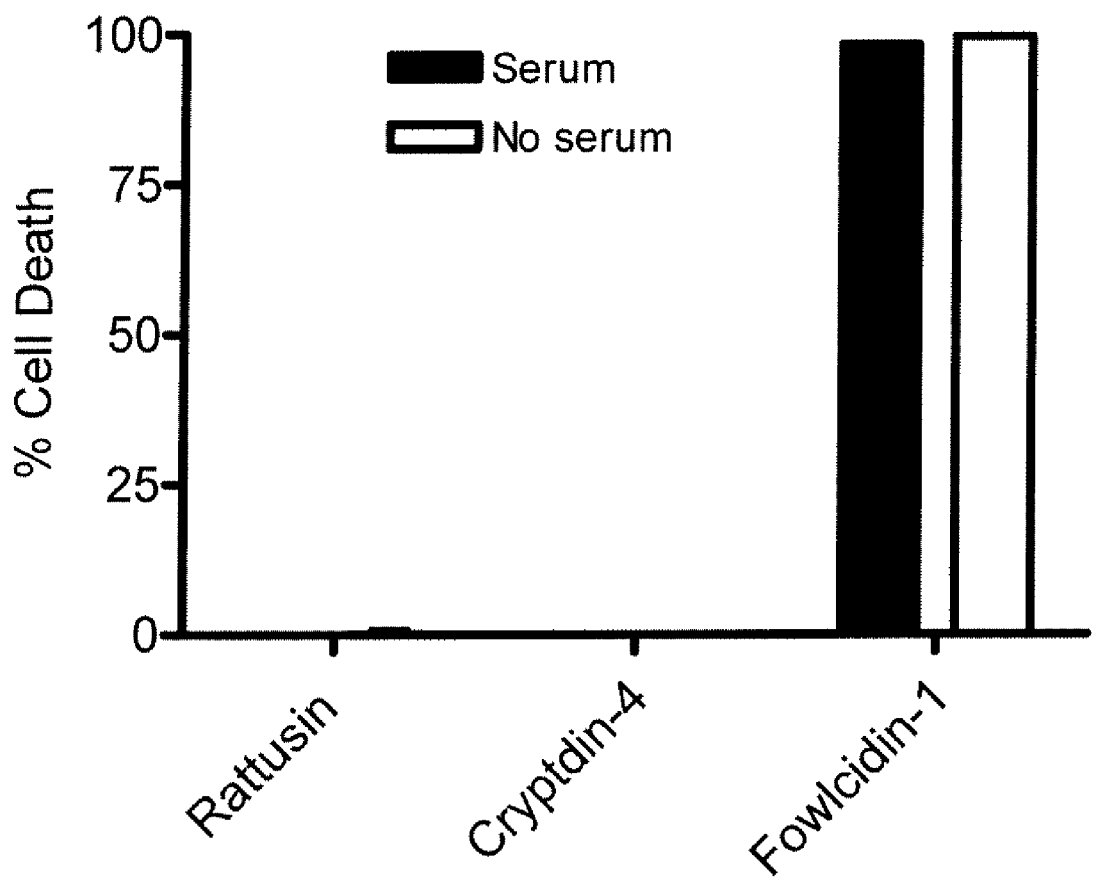
FIG. 8. Absence of cytotoxicity of rattusin and cryptdin-4 to Caco-2 cells. Cells were incubated with 100 µM of rattusin, cryptdin-4 or fowlicidin-1 for 24 h in DMEM with and without 10% fetal bovine serum for 24 hours. Cell viability was measured with an alamarBlue dye-based method. Data are representative of two independent experiments done in duplicate.

The cytotoxic effect of rattusin to intestinal epithelial cells was studied using human Caco-2 cells. Fowlicidin-1 (100 μM) was used as a positive reference since it showed significant cytotoxicity towards mammalian cells (26). Following treatment of cells for 24 h, rattusin exhibited no cytotoxicity even at 100 μM, similar to cryptdin-4 (FIG. 8).

DISCUSSION

Rattusin shares a highly conserved signal and pro-sequence with classical mammalian a-defensins, but with a unique C-terminal region (FIG. 1). The results presented in this Example demonstrate that this C-terminal peptide possesses potent, broad-spectrum antibacterial activities. Recently, a number of cysteine-rich cryptdin-related sequences (CRS) in mice were described and also share a highly homologous prepro-region to mice cryptdins (14). However, the cysteine-spacing patterns of these CRS peptides are also different from those of rattusin.

Desirably, rattusin maintains its antibacterial activity in the presence of physiological concentrations of NaCl, which is in sharp contrast to cryptdin-4, HD-5, and other defensins, which show reduced antibacterial activity in the presence of NaCl (3, 4, 8, 38). Maintenance of the antibacterial activity of rattusin in the presence of salt might be due to its high cationicity (with net charge of +8) and the structural properties provided by the unique cysteine spacing pattern, which is different from the classical α-defensins. Cryptdin-4 disrupts bilayer head groups through ionic interactions between the positively charged peptide and negatively charged lipids (24, 39). Such an interaction is more susceptible to inhibition by physiological concentrations of NaCl, which in rodent ileum is maintained at around 162 mM (40). Since rattusin is relatively resistant to NaCl, its mechanism of action is likely to be different from that of cryptdin-4.

Divalent cations such as $Mg^{2+}$ stabilize liposaccharide (LPS) of Gram-negative bacteria by binding to negatively charged phosphate and pyrophosphate groups of LPS, thereby preventing charge-charge repulsion (19, 41). Antimicrobial peptides must displace these divalent cations in order to interact with the outer membrane (19, 41). A number of defensins and cathelicidins are inhibited at physiological concentrations of divalent cations (36, 37, 42-44). Rattusin kills bacteria in the presence of 2-5 mM $Mg^{2+}$, whereas cryptdin-4 is inactivated, suggesting that rattusin is capable of displacing divalent cations.

Divalent cations do not inhibit the efficacy of cationic antimicrobial peptides against Gram-positive bacteria since they lack LPS. On the contrary, $Mg^{2+}$ potentiated the activity of rattusin against *S. aureus*. However, this finding is not surprising since $Mg^{2+}$ causes transcriptional suppression of the dlt operon in *S. aureus* (45). The dlt operon is involved in incorporation of D-alanine into lipoteichoic acid and wall teichoic acid, which introduces positively charged amino group and partially neutralizes negative charges on teichoic acid, thereby providing resistance to cationic antimicrobial peptides (46). Therefore, suppression of dlt operon by $Mg^{2+}$ increases susceptibility of *S. aureus* to cationic rattusin and cryptdin-4.

In conclusion, rattusin is unique α-defensin-related peptide, which is preferentially expressed in distal small intestine. It possesses broad-spectrum antibacterial activity that is insensitive to salt and divalent cations. The salt-insensitive activity of rattusin may be further exploited for the treatment of cystic fibrosis and Crohn's disease. Increased salt concentrations are believed to be responsible for inactivation of defensins in the airway of the cystic fibrosis patients (47). In Crohn's disease, a deficiency of intestinal Paneth cell defensins is associated with an increase in susceptibility to bacterial infections (48). Therefore, exogenous delivery of potent, salt-insensitive rattusin represents a promising therapeutic strategy to treat both topical and systemic antibiotic-resistant infections.

REFERENCES

1. Gonzales, R., D. C. Malone, J. H. Maselli, and M. A. Sande. 2001. Excessive antibiotic use for acute respiratory infections in the United States. Clin Infect Dis 33:757-762.
2. Finch, R. G. 2004. Antibiotic resistance: a view from the prescriber. Nat Rev Microbiol 2:989-994.
3. Selsted, M. E., and A. J. Ouellette. 2005. Mammalian defensins in the antimicrobial immune response. Nat Immunol 6:551-557.
4. Ganz, T. 2003. Defensins: antimicrobial peptides of innate immunity. Nat Rev Immunol 3:710-720.
5. Froy, O., and M. Gurevitz. 2003. Arthropod and mollusk defensins—evolution by exon-shuffling. Trends Genet. 19:684-687.
6. Thomma, B. P., B. P. Cammue, and K. Thevissen. 2002. Plant defensins. Planta 216:193-202.
7. Lehrer, R. I., and T. Ganz. 2002. Defensins of vertebrate animals. Curr Opin Immunol 14:96-102.
8. Lehrer, R. I. 2004. Primate defensins. Nat Rev Microbiol 2:727-738.
9. Ouellette, A. J. 2004. Defensin-mediated innate immunity in the small intestine. Best Pract Res Clin Gastroenterol 18:405-419.
10. Salzman, N. H., M. A. Underwood, and C. L. Bevins. 2007. Paneth cells, defensins, and the commensal microbiota: A hypothesis on intimate interplay at the intestinal mucosa. Seminars in immunology 19:70-83.
11. Pazgier, M., D. M. Hoover, D. Yang, W. Lu, and J. Lubkowski. 2006. Human beta-defensins. Cell Mol Life Sci 63:1294-1313.
12. Huttner, K. M., and A. J. Ouellette. 1994. A family of defensin-like genes codes for diverse cysteine-rich peptides in mouse Paneth cells. Genomics 24:99-109.
13. Ouellette, A. J., and J. C. Lualdi. 1990. A novel mouse gene family coding for cationic, cysteine-rich peptides. Regulation in small intestine and cells of myeloid origin. J Biol Chem 265:9831-9837.
14. Hornef, M. W., K. Putsep, J. Karlsson, E. Refai, and M. Andersson. 2004. Increased diversity of intestinal antimicrobial peptides by covalent dimer formation. Nature immunology 5:836-843.
15. Ghosh, D., E. Porter, B. Shen, S. K. Lee, D. Wilk, J. Drazba, S. P. Yadav, J. W. Crabb, T. Ganz, and C. L. Bevins. 2002. Paneth cell trypsin is the processing enzyme for human defensin-5. Nature Immunology 3:583-590.
16. Wilson, C. L., A. J. Ouellette, D. P. Satchell, T. Ayabe, Y. S. Lopez-Boado, J. L. Stratman, S. J. Hultgren, L. M. Matrisian, and W. C. Parks. 1999. Regulation of intestinal alpha-defensin activation by the metalloproteinase matrilysin in innate host defense. Science 286:113-117.
17. Ayabe, T., D. P. Satchell, P. Pesendorfer, H. Tanabe, C. L. Wilson, S. J. Hagen, and A. J. Ouellette. 2002. Activation of Paneth cell alpha-defensins in mouse small intestine. J Biol Chem 277:5219-5228.

18. Yang, D., A. Biragyn, D. M. Hoover, J. Lubkowski, and J. J. Oppenheim. 2004. Multiple roles of antimicrobial defensins, cathelicidins, and eosinophil-derived neurotoxin in host defense. Annu Rev Immunol 22:181-215.
19. McPhee, J. B., and R. E. Hancock. 2005. Function and therapeutic potential of host defense peptides. J Pept Sci 11:677-687.
20. Bowdish, D. M., D. J. Davidson, and R. E. Hancock. 2005. A re-evaluation of the role of host defense peptides in mammalian immunity. Curr Protein Pept Sci 6:35-51.
21. Zhang, L., and T. J. Falla. 2006. Antimicrobial peptides: therapeutic potential. Expert Opin Pharmacother 7:653-663.
22. Patil, A., A. L. Hughes, and G. Zhang. 2004. Rapid evolution and diversification of mammalian alpha-defensins as revealed by comparative analysis of rodent and primate genes. Physiol Genomics 20:1-11.
23. Shirafuji, Y., H. Tanabe, D. P. Satchell, A. Henschen-Edman, C. L. Wilson, and A. J. Ouellette. 2003. Structural determinants of procryptdin recognition and cleavage by matrix metalloproteinase-7. J Biol Chem 278:7910-7919.
24. Satchell, D. P., T. Sheynis, Y. Shirafuji, S. Kolusheva, A. J. Ouellette, and R. Jelinek. 2003. Interactions of mouse Paneth cell alpha-defensins and alpha-defensin precursors with membranes. Prosegment inhibition of peptide association with biomimetic membranes. J Biol Chem 278: 13838-13846.
25. Wu, Z., B. Ericksen, K. Tucker, J. Lubkowski, and W. Lu. 2004. Synthesis and characterization of human alpha-defensins 4-6. J Pept Res 64:118-125.
26. Xiao, Y., Y. Cai, Y. R. Bommineni, S. C. Fernando, O. Prakash, S. E. Gilliland, and G. Zhang. 2006. Identification and functional characterization of three chicken cathelicidins with potent antimicrobial activity. J Biol Chem 281: 2858-2867.
27. Xiao, Y., H. Dai, Y. R. Bommineni, J. L. Soulages, Y.-X. Gong, O. Prakash, and G. Zhang. 2006. Structure-activity relationships of fowlicidin-1, a cathelicidin antimicrobial peptide in chicken. FEBS J 273:2581-2593.
28. Xiao, Y., A. L. Hughes, J. Ando, Y. Matsuda, J. F. Cheng, D. Skinner-Noble, and G. Zhang. 2004. A genome-wide screen identifies a single beta-defensin gene cluster in the chicken: implications for the origin and evolution of mammalian defensins. BMC Genomics 5:56.
29. Patil, A. A., Y. Cai, Y. Sang, F. Blecha, and G. Zhang. 2005. Cross-species analysis of the mammalian beta-defensin gene family: presence of syntenic gene clusters and preferential expression in the male reproductive tract. Physiol Genomics 23:5-17.
30. Darmoul, D., and A. J. Ouellette. 1996. Positional specificity of defensin gene expression reveals Paneth cell heterogeneity in mouse small intestine. Am. J. Physiol 271: G68-G74.
31. Ouellette, A. J., D. Darmoul, D. Tran, K. M. Huttner, J. Yuan, and M. E. Selsted. 1999. Peptide localization and gene structure of cryptdin 4, a differentially expressed mouse paneth cell alpha-defensin. Infect Immun 67:6643-6651.
32. Wehkamp, J., H. Chu, B. Shen, R. W. Feathers, R. J. Kays, S. K. Lee, and C. L. Bevins. 2006. Paneth cell antimicrobial peptides: topographical distribution and quantification in human gastrointestinal tissues. FEBS Lett 580:5344-5350.
33. Wu, Z., A. Prahl, R. Powell, B. Ericksen, J. Lubkowski, and W. Lu. 2003. From pro defensins to defensins: synthesis and characterization of human neutrophil pro alpha-defensin-1 and its mature domain. J Pept Res 62:53-62.
34. Wu, Z., R. Powell, and W. Lu. 2003. Productive folding of human neutrophil alpha-defensins in vitro without the propeptide. J Am Chem Soc 125:2402-2403.
35. Bowdish, D. M., D. J. Davidson, and R. E. Hancock. 2006. Immunomodulatory properties of defensins and cathelicidins. Curr Top Microbiol Immunol 306:27-66.
36. Friedrich, C., M. G. Scott, N. Karunaratne, H. Yan, and R. E. Hancock. 1999. Salt-resistant alpha-helical cationic antimicrobial peptides. Antimicrob Agents Chemother 43:1542-1548.
37. Bowdish, D. M., D. J. Davidson, Y. E. Lau, K. Lee, M. G. Scott, and R. E. Hancock. 2005. Impact of LL-37 on anti-infective immunity. J Leukoc Biol 77:451-459.
38. Porter, E. M., E. van Dam, E. V. Valore, and T. Ganz. 1997. Broad-spectrum antimicrobial activity of human intestinal defensin 5. Infect Immun 65:2396-2401.
39. Satchell, D. P., T. Sheynis, S. Kolusheva, J. Cummings, T. K. Vanderlick, R. Jelinek, M. E. Selsted, and A. J. Ouellette. 2003. Quantitative interactions between cryptdin-4 amino terminal variants and membranes. Peptides 24:1795-1805.
40. Miller, D. L., S. A. Hamburger, and H. P. Schedl. 1979. Effects of osmotic gradients on water and solute transport: in vivo studies in rat duodenum and ileum. Am J Physiol 237:E389-396.
41. Hancock, R. E., and M. G. Scott. 2000. The role of antimicrobial peptides in animal defenses. Proc Natl Acad Sci USA 97:8856-8861.
42. Krishnakumari, V., S. Singh, and R. Nagaraj. 2006. Antibacterial activities of synthetic peptides corresponding to the carboxy-terminal region of human beta-defensins 1-3. Peptides 27:2607-2613.
43. Lehrer, R. I., T. Ganz, D. Szklarek, and M. E. Selsted. 1988. Modulation of the in vitro candidacidal activity of human neutrophil defensins by target cell metabolism and divalent cations. J Clin Invest 81:1829-1835.
44. Anderson, R. C., and P. L. Yu. 2005. Factors affecting the antimicrobial activity of ovine-derived cathelicidins against E. coli O157:H7. Int J Antimicrob Agents 25:205-210.
45. Koprivnjak, T., V. Mlakar, L. Swanson, B. Fournier, A. Peschel, and J. P. Weiss. 2006. Cation-induced transcriptional regulation of the dlt operon of Staphylococcus aureus. Bacteriol 188:3622-3630.
46. Kraus, D., and A. Peschel. 2006. Molecular mechanisms of bacterial resistance to antimicrobial peptides. Curr Top Microbiol Immunol 306:231-250.
47. Goldman, M. J., G. M. Anderson, E. D. Stolzenberg, U. P. Kari, M. Zasloff, and J. M. Wilson. 1997. Human beta-defensin-1 is a salt-sensitive antibiotic in lung that is inactivated in cystic fibrosis. Cell 88:553-560.
48. Peyrin-Biroulet, L., C. Vignal, R. Dessein, M. Simonet, P. Desreumaux, and M. Chamaillard. 2006. NODs in defense: from vulnerable antimicrobial peptides to chronic inflammation. Trends in Microbiology 14:432-438.
49. Sitaram, N., and R. Nagaraj. 2002. Host-defense antimicrobial peptides: importance of structure for activity. Curr Pharm Des 8:727-742.
50. Schibli, D. J., H. N. Hunter, V. Aseyev, T. D. Starner, J. M. Wiencek, P. B. McCray, Jr., B. F. Tack, and H. J. Vogel. 2002. The solution structures of the human beta-defensins lead to a better understanding of the potent bactericidal activity of HBD3 against Staphylococcus aureus. J Biol Chem 277:8279-8289.

51. Raj, P. A., K. J. Antonyraj, and T. Karunakaran. 2000. Large-scale synthesis and functional elements for the antimicrobial activity of defensins. Biochem. J. 347 Pt 3:633-641.
52. Tanabe, H., X. Qu, C. S. Weeks, J. E. Cummings, S. Kolusheva, K. B. Walsh, R. Jelinek, T. K. Vanderlick, M. E. Selsted, and A. J. Ouellette. 2004. Structure-activity determinants in paneth cell alpha-defensins: loss-of-function in mouse cryptdin-4 by charge-reversal at arginine residue positions. J Biol Chem 279:11976-11983.

Example 2

Rational Design of Rattusin Analogs

Preliminary studies with rattusin revealed that the reduced peptide showed similar antibacterial efficacy to the refolded form in low concentrations of salt, but lost significant activities in high salt (data not shown), suggesting that the presence of disulfide bonds and intact β-sheet structure are critical in maintaining the salt-independent activity. Similar to several α- and β-defensins (49-52), the central cysteine-rich motif of rattusin is flanked by long flexible N- and C-terminal tails, which are primarily composed of charged and uncharged polar residues (Table 2). The impact of N- and C-terminal tails and five cysteines of rattusin on its antibacterial, cytotoxic, chemotactic, and immuno-modulatory functions is investigated.

Generation of Deletion Variants of Rattusin.

The long N- and C-terminal tails are sequentially deleted to reveal their functional relevance (Table 2). Based on the results obtained, partial gradual deletions and substitutions of N- and C-terminal tail sequences are performed with the tail(s) that have a profound impact on the functions of rattusin.

Substitution of Six Cysteines.

To further confirm the impact of intact disulfide bonds on the antibacterial activity and to minimize the complications of possible peptide oxidation during incubation with bacteria, a linear variant with all five cysteines being replaced with alanines is synthesized (Table 2). To pinpoint the relative significance of each disulfide bond in maintaining salt-independent antibacterial potency and the overall structure, individual pairs of cysteines forming a disulfide bond are sequentially mutated to alanines to generate defensins with only one or two disulfide bonds. Based on the 3-D structure of native rattusin, the amino acids that are involved in maintaining its overall structure or forming patches of polar or hydrophobic pockets are mutated to change its conformation and/or amphipathicity. All peptide analogs are synthesized with and without incorporation of an amide group at the C-terminal end. Additional analogs are made based on the functional activities of these analogs.

TABLE 2

Rational Design of Rattusin and Its Analogs

| PEPTIDE | SEQUENCE* | SEQ ID NO: |
|---|---|---|
| Rattusin | LRVRRTLQCSCRRVCRNTCSCIRLSRSTYAS | 1 |
| RSNΔN6 | LQCSCRRVCRNTCSCIRLSRSTYAS | 2 |
| RSNΔC9 | LRVRRTLQCSCRRVCRNTCSCI | 3 |
| RSNΔC5 | LRVRRTLQCSCRRVCRNTCSCIRLSR | 4 |
| RSNΔN6ΔC9 | LQCSCRRVCRNTCSCI | 5 |
| RSN-Linear | LRVRRTLQASARRVARNTASAIRLSRSTYAS | 6 |

*Cysteines and replacement alanines shown in bold and underlined.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A substantially purified peptide consisting of the amino acid sequence set forth in SEQ ID NO: 1.

2. A composition having antibacterial activity under physiological conditions, comprising a peptide consisting of the amino acid sequence set forth in SEQ ID NO: 1.

3. The antibacterial composition of claim 2, wherein said antimicrobial composition has a salt concentration in the range of from 0 to 250 mM salt.

4. The antibacterial composition of claim 3, wherein said salt is NaCl or KCl, or both.

5. The antibacterial composition of claim 3, wherein said salt concentration is at least 50 mM.

6. The antimicrobial composition of claim 2, wherein said antimicrobial composition has a divalent cation concentration in the range of from 0 to 5 mM.

7. The antibacterial of claim 6, wherein said divalent cation is $Mg^{+2}$ or $Ca^{+2}$, or both.

8. The antibacterial composition of claim 6, wherein said divalent cation concentration is at least 1 mM.

* * * * *